United States Patent
Gui et al.

(10) Patent No.: US 10,758,143 B2
(45) Date of Patent: Sep. 1, 2020

(54) BLOOD PRESSURE PARAMETER DETECTION METHOD AND USER EQUIPMENT

(71) Applicant: HUAWEI TECHNOLOGIES CO., LTD., Shenzhen (CN)

(72) Inventors: Yonglin Gui, Shenzhen (CN); Bo Yang, Shenzhen (CN); Qizhi Zhan, Shenzhen (CN); Honggang Li, Shenzhen (CN); Zexu Qian, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 56 days.

(21) Appl. No.: 15/779,088

(22) PCT Filed: Nov. 26, 2015

(86) PCT No.: PCT/CN2015/095717
§ 371 (c)(1),
(2) Date: May 25, 2018

(87) PCT Pub. No.: WO2017/088156
PCT Pub. Date: Jun. 1, 2017

(65) Prior Publication Data
US 2018/0344193 A1    Dec. 6, 2018

(51) Int. Cl.
*A61B 5/0408* (2006.01)
*A61B 5/0456* (2006.01)
(Continued)

(52) U.S. Cl.
CPC ...... *A61B 5/04085* (2013.01); *A61B 5/02116* (2013.01); *A61B 5/02125* (2013.01);
(Continued)

(58) Field of Classification Search
USPC ........................................................ 600/513
See application file for complete search history.

(56) References Cited

U.S. PATENT DOCUMENTS 6,647,287 B1 * 11/2003 Peel, III ............. A61B 5/02125
600/485
9,808,206 B1 * 11/2017 Zhao ................. A61B 5/7282
(Continued)

FOREIGN PATENT DOCUMENTS

CN         1548006 A    11/2004
CN       101264011 A     9/2008
(Continued)

OTHER PUBLICATIONS

Sophia,"Wello: Use your phone to measure blood pressure, heart rate, and body Temperature", dated Mar. 10, 2014,total 9 pages.

*Primary Examiner* — Gary Jackson
*Assistant Examiner* — Zahed Kabir
(74) *Attorney, Agent, or Firm* — Kilpatrick Townsend & Stockton LLP

(57) ABSTRACT

Embodiments disclose a blood pressure parameter detection method. The method includes: detecting, by user equipment UE, an electrocardiogram ECG signal of a user by using a first ECG contact and a second ECG contact that are connected to an ECG detection circuit of the UE; when determining that the detected ECG signal matches a pre-stored reference ECG signal, enabling, by the UE, a photoplethysmogram PPG detection circuit, and detecting a PPG signal of the user by using a PPG detection point connected to the PPG detection circuit; and when determining that the detected PPG signal matches a pre-stored reference PPG signal, enabling, by the UE, a blood pressure detection application, and processing the detected ECG signal and the detected PPG signal by using the blood pressure detection application to obtain a blood pressure parameter of the user.

6 Claims, 7 Drawing Sheets

(51) Int. Cl.
  *A61B 5/04* (2006.01)
  *A61B 5/00* (2006.01)
  *A61B 5/021* (2006.01)
  *A61B 5/024* (2006.01)
  *H04M 1/725* (2006.01)
  *A61B 5/0452* (2006.01)
  *A61B 5/1172* (2016.01)

(52) U.S. Cl.
  CPC ...... *A61B 5/02416* (2013.01); *A61B 5/04012* (2013.01); *A61B 5/0452* (2013.01); *A61B 5/0456* (2013.01); *A61B 5/6843* (2013.01); *A61B 5/6898* (2013.01); *A61B 5/7221* (2013.01); *H04M 1/725* (2013.01); *A61B 5/1172* (2013.01); *A61B 5/7278* (2013.01); *A61B 5/742* (2013.01)

(56) References Cited

U.S. PATENT DOCUMENTS

| | | | |
|---|---|---|---|
| 2008/0228089 A1 | 9/2008 | Cho et al. | |
| 2009/0281399 A1* | 11/2009 | Keel | A61B 5/02158 600/301 |
| 2011/0224508 A1* | 9/2011 | Moon | A61B 5/0002 600/301 |
| 2012/0029320 A1* | 2/2012 | Watson | A61B 5/02125 600/301 |
| 2014/0012146 A1* | 1/2014 | Fukuda | A61B 5/02125 600/485 |
| 2014/0031646 A1* | 1/2014 | Yakirevich | A61B 5/7239 600/310 |
| 2015/0119725 A1* | 4/2015 | Martin | A61B 5/04012 600/479 |
| 2015/0313484 A1 | 11/2015 | Burg et al. | |
| 2015/0313486 A1 | 11/2015 | Mestha et al. | |
| 2015/0320328 A1* | 11/2015 | Albert | A61B 5/0402 600/480 |
| 2017/0079591 A1* | 3/2017 | Gruhlke | A61B 5/6898 |

FOREIGN PATENT DOCUMENTS

| | | |
|---|---|---|
| CN | 201617817 U | 11/2010 |
| CN | 102008296 A | 4/2011 |
| CN | 103519794 A | 1/2014 |
| CN | 104323764 A | 2/2015 |
| CN | 104856661 A | 8/2015 |
| WO | 2015061166 A1 | 4/2015 |
| WO | 2015121689 A1 | 8/2015 |
| WO | 2015171764 A1 | 11/2015 |

* cited by examiner

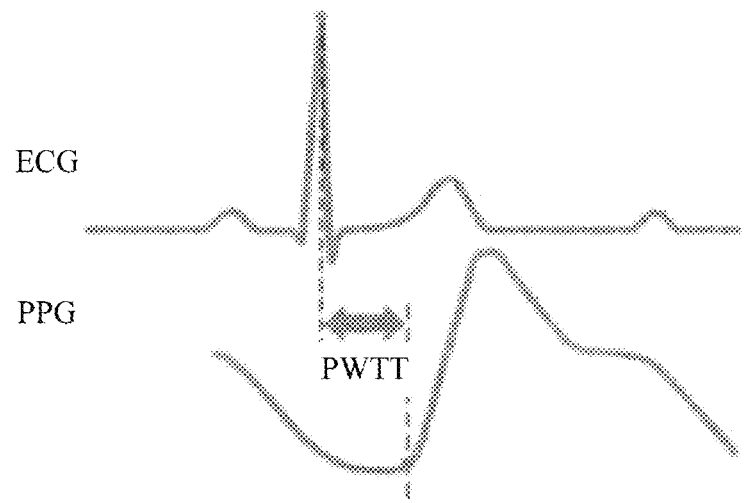
FIG. 1.1
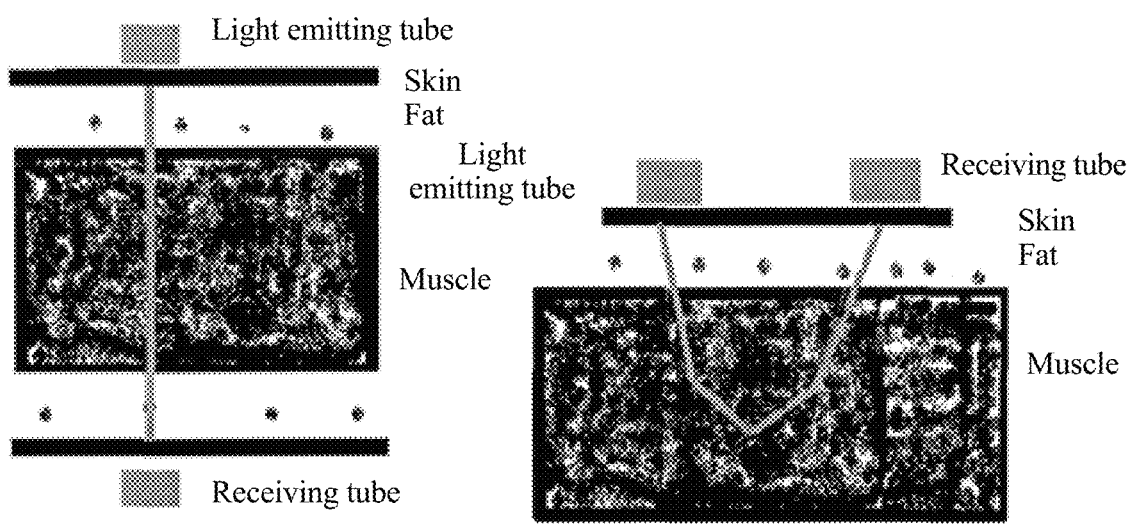
FIG. 1.2

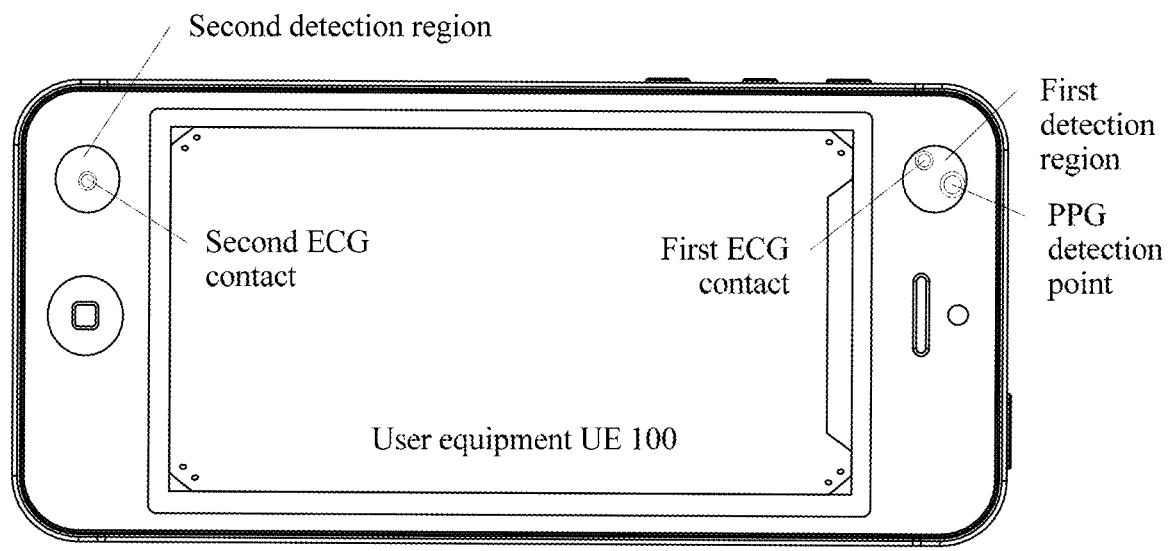
FIG. 2.1
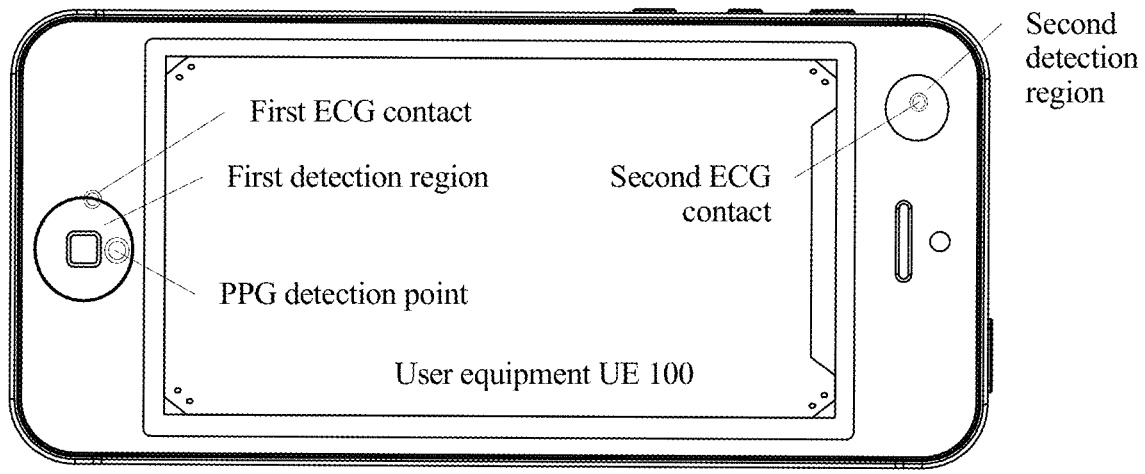
FIG. 2.2

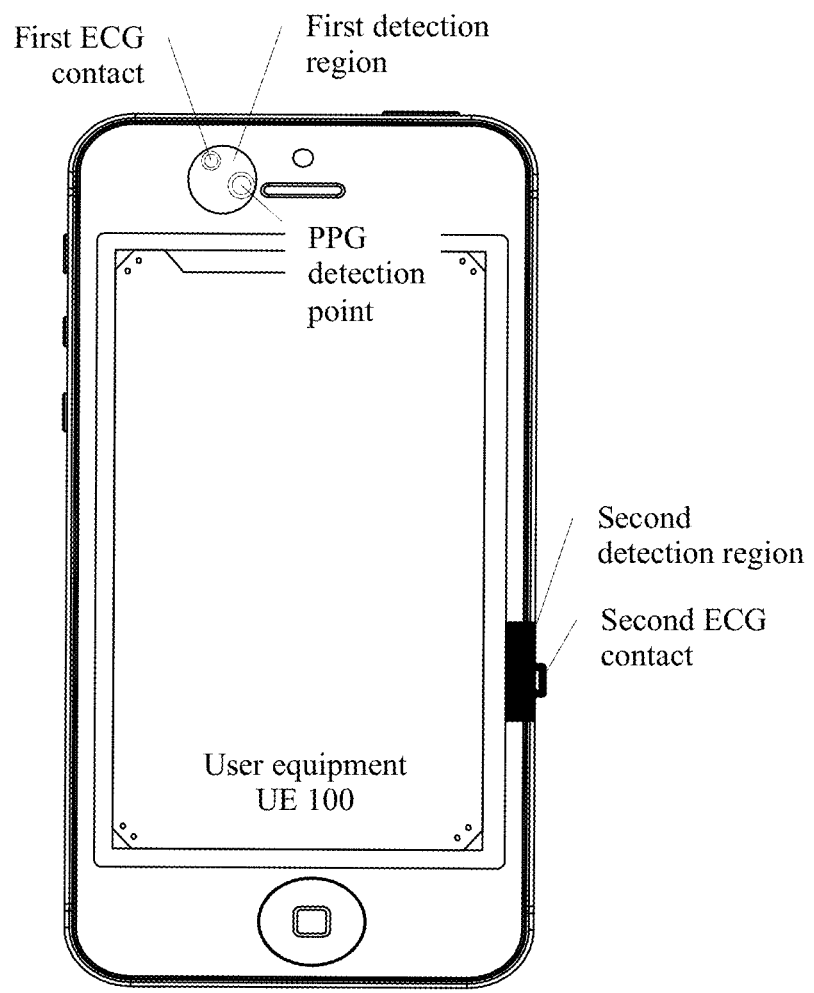
FIG. 2.3

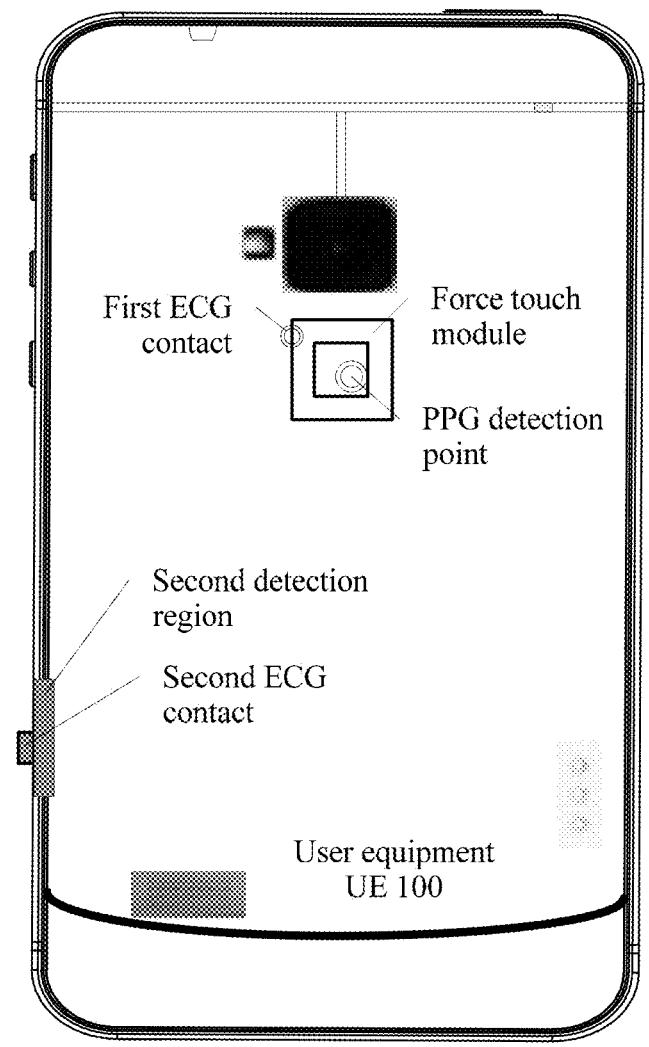
FIG. 3.1

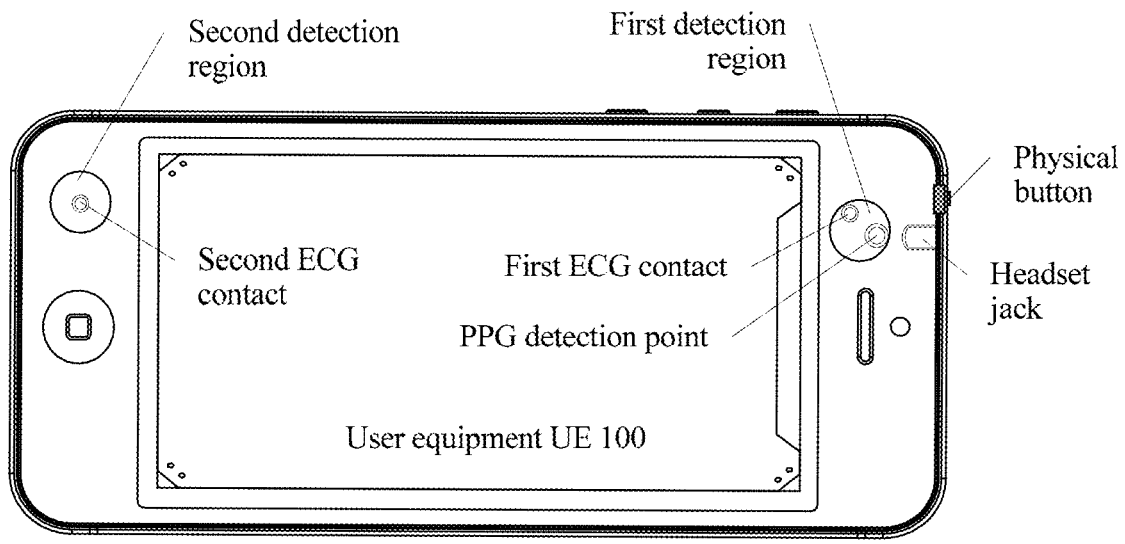
FIG. 3.2
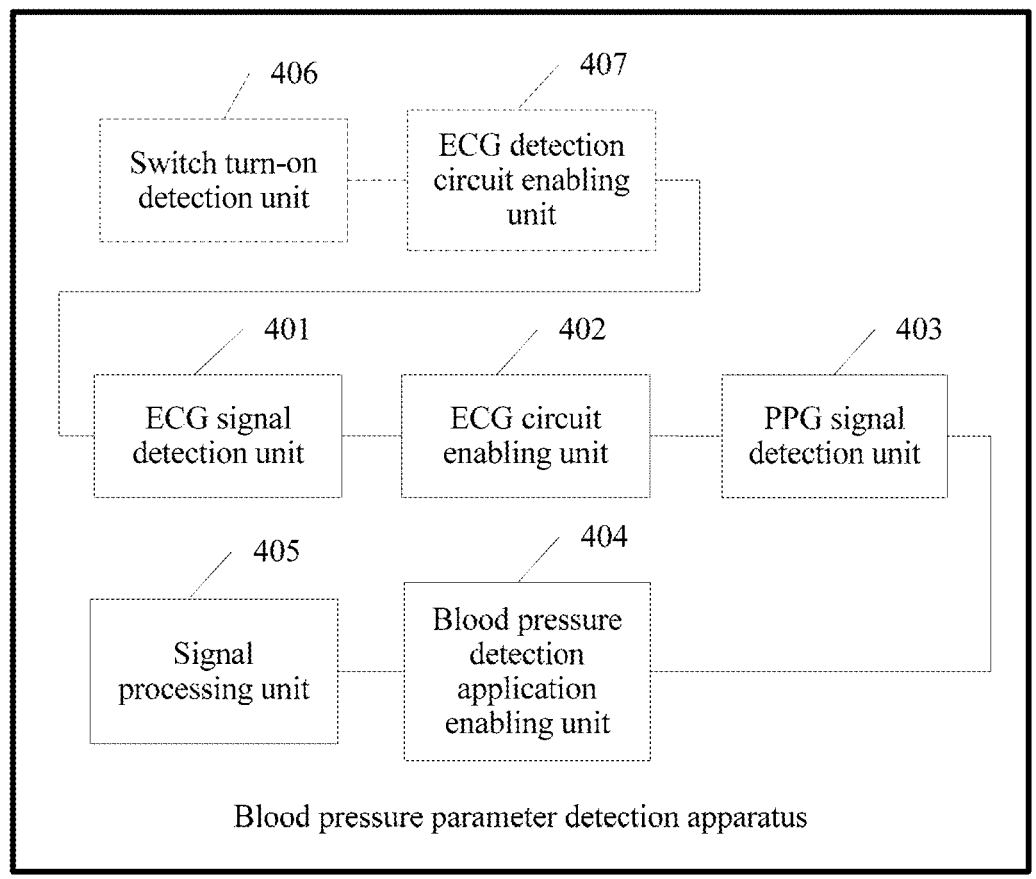
FIG. 4

BLOOD PRESSURE PARAMETER DETECTION METHOD AND USER EQUIPMENT

CROSS-REFERENCE TO RELATED APPLICATIONS

This application is a National Stage of International Application No. PCT/CN2015/095717, filed on Nov. 26, 2015, which is hereby incorporated by reference in its entirety.

TECHNICAL FIELD

The present invention relates to the field of electronic technologies, and specifically, to a blood pressure parameter detection method and user equipment.

BACKGROUND

A pulse wave transit time (Pulse wave transit time, PWTT) measurement method is used in an existing terminal product for blood pressure measurement, for example, a product of combining a tablet computer with a sphygmomanometer or a product of combining a smartphone with a cell phone case for blood pressure detection. When a user uses such a terminal product to measure blood pressure, the user usually needs to perform the following operations: unlocking a primary device→opening an application-→establishing a communication connection to a secondary device→selecting a parameter (for example, selecting a user)→starting measurement→placing a hand at a measurement point according to a prompt message. In this case, the device completes measurement and displays a measurement result.

In a research process, the inventor of the present invention finds that the foregoing blood pressure measurement solution involves complex operations and tedious steps, and therefore is not easy to learn and master. The elderly group is usually a main object of blood pressure measurement, and it is difficult for the elderly to quickly learn and master the foregoing blood pressure measurement method. In addition, in the existing blood pressure detection solution, when a user unsteadily touches a detection point, a terminal device can collect a related signal and output a blood pressure parameter. Consequently, accuracy of a detection result of a blood pressure parameter is affected.

SUMMARY

Embodiments of the present invention provide a blood pressure detection method and user equipment, so as to improve blood pressure detection convenience and accuracy of the user equipment.

A first aspect of embodiments of the present invention discloses a blood pressure parameter detection method, including:

detecting, by user equipment UE, an electrocardiogram ECG signal of a user by using a first ECG contact and a second ECG contact that are connected to an ECG detection circuit of the UE, where the first ECG contact and the second ECG contact form a pair of detection electrodes;

when determining that the detected ECG signal matches a prestored reference ECG signal, enabling, by the UE, a photoplethysmogram PPG detection circuit, and detecting a PPG signal of the user by using a PPG detection point connected to the PPG detection circuit; and when determining that the detected PPG signal matches a prestored reference PPG signal, enabling, by the UE, a blood pressure detection application, and processing the detected ECG signal and the detected PPG signal by using the blood pressure detection application to obtain a blood pressure parameter of the user.

In a first possible implementation of the first aspect of the embodiments of the present invention, an area of a first detection region formed by the PPG detection point and the first ECG contact is less than a preset area threshold; and the second ECG contact is disposed in a second detection region of the UE, and the first detection region is different from the second detection region. For example, the preset area may be an average area of fingertip surfaces of adults, so that a user can simultaneously touch the PPG detection point and the first ECG contact by using only one finger. Such setting helps reduce a quantity of touch locations between the user and detection points and improve stability of touching the ECG detection points and the PPG detection point by the user, thereby improving blood pressure parameter detection accuracy of the UE.

The second ECG contact is disposed in a second detection region of the UE, and the first detection region is different from the second detection region.

With reference to the first aspect or the first possible implementation of the first aspect of the embodiments of the present invention, in a second possible implementation of the first aspect of the embodiments of the present invention, before the detecting, by UE, an electrocardiogram ECG signal of a user by using a first ECG contact and a second ECG contact that are connected to an ECG detection circuit of the UE, the method further includes:

detecting, by the UE, an enabling operation instruction that is of the user and for an enabling switch of the ECG detection circuit of the UE; where the ECG detection circuit connects the first ECG contact and the second ECG contact, the enabling switch of the ECG detection circuit includes at least one of the following: a force touch module, a physical button, or a fingerprint recognition module; and enabling, by the UE, the ECG detection circuit when detecting the enabling operation instruction that is of the user and for the enabling switch of the ECG detection circuit of the UE.

A second aspect of embodiments of the present invention discloses user equipment UE for blood pressure detection, and the UE includes a memory and a processor coupled to the memory. The memory is configured to store an instruction, and the processor is configured to run the instruction. The processor runs the instruction, so as to perform some or all steps of any method in the first aspect of the embodiments of the present invention.

A third aspect of embodiments of the present invention discloses a computer readable storage medium, the computer readable storage medium stores program code that needs to be executed when user equipment UE is applied to blood pressure detection, and the program code specifically includes an instruction for performing some or all steps of any method in the first aspect of the embodiments of the present invention.

A fourth aspect of embodiments of the present invention discloses user equipment UE for blood pressure detection, and the UE includes functional units for performing some or all steps of any method in the first aspect of the embodiments of the present invention.

In some possible implementations, the first detection region is on an upper frame of the UE, and the second detection region is on a lower frame of the UE.

In some possible implementations, the first detection region is at a location of a fingerprint recognition module of the UE, and the second detection region is on an upper frame of the UE. The first ECG contact is disposed on a metal drive ring or a metal frame of the fingerprint recognition module, and the PPG detection point is disposed in a radiofrequency sensing electrode array of the fingerprint recognition module.

In some possible implementations, the first detection region is at a preset location near an earpiece of the UE, and the second detection region is on a side frame of the UE. When a user answers a call, and a palm of the user touches the side frame of the UE, the palm of the user touches the second detection region, and a part (for example, an earlobe) of an ear of the user touches the first detection region. In this way, when the user is in a call, the UE may measure a blood pressure parameter of the user, thereby improving blood pressure detection convenience of the UE.

In some possible implementations, when the enabling switch of the ECG detection circuit includes the force touch module of the UE, the detecting, by the UE, an enabling operation instruction that is of the user and for an enabling switch of the ECG detection circuit of the UE includes: detecting, by the UE, that a force parameter entered by the user by using the force touch module matches a preset force parameter.

In some possible implementations, when the enabling switch of the ECG detection circuit includes the physical button that is disposed at a preset location of the UE and that is configured to enable the ECG detection circuit, the detecting, by the UE, an enabling operation instruction that is of the user and for an enabling switch of the ECG detection circuit of the UE includes: capturing, by the UE, an enabling operation event that is of the user and for the physical button, where the physical button is disposed at the preset location of the UE and configured to enable the ECG detection circuit.

In some possible implementations, when the enabling switch of the ECG detection circuit includes the fingerprint recognition module of the UE, the detecting, by the UE, an enabling operation instruction that is of the user and for an enabling switch of the ECG detection circuit of the UE includes: detecting, by the UE, that fingerprint data entered by the user by using the fingerprint recognition module matches preset fingerprint data.

In the embodiments of the present invention, UE first detects an ECG signal of a user by using a first ECG contact and a second ECG contact; next, when determining that the detected ECG signal matches a prestored reference ECG signal, the UE enables a PPG detection circuit of the UE, and detects a PPG signal of the user by using a PPG detection point connected to the PPG detection circuit; then, when determining that the detected PPG signal matches a prestored reference PPG signal, the UE enables a blood pressure detection application of the UE, and processes the detected ECG signal and the detected PPG signal by using the blood pressure detection application to obtain a blood pressure parameter of the user.

In the foregoing blood pressure parameter detection process of the UE, when detecting that the obtained ECG signal matches the prestored reference ECG signal, the UE may enable the PPG detection circuit of the UE, and when detecting that the obtained PPG signal matches the prestored reference PPG signal, the UE may enable the blood pressure detection application of the UE. It may be learned that in the foregoing blood pressure parameter detection process of the UE, the user does not need to perform complex setting operations, thereby improving blood pressure detection convenience of the UE.

In addition, in the foregoing blood pressure detection process, the UE needs to detect that the obtained ECG signal matches the prestored reference ECG signal, so as to enable the PPG detection circuit, and needs to detect that the obtained PPG signal matches the prestored reference PPG signal, so as to enable the blood pressure detection application of the UE. The matched ECG signal and the matched PPG signal are corresponding to a state in which the user steadily touches the ECG detection points and the PPG detection point, so that both the ECG signal and the PPG signal processed after the UE enables the blood pressure detection application are signals obtained when the user steadily touches a detection point. Therefore, error signals entered by the user in an unsteady touch state can be reduced, thereby improving blood pressure detection accuracy of the UE.

BRIEF DESCRIPTION OF DRAWINGS

To describe the technical solutions in the embodiments of the present invention or in the prior art more clearly, the following briefly describes the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

FIG. 1.1 is a schematic diagram of calculating a PWTT based on a PPG wave and an ECG wave disclosed in an embodiment of the present invention;

FIG. 1.2 is a schematic diagram of collecting light intensity on the body surface by a transmissive photoelectric sensor and a reflective photoelectric sensor disclosed in an embodiment of the present invention;

FIG. 2.1 is a schematic diagram of location combination of a first detection region and a second detection region disclosed in an embodiment of the present invention;

FIG. 2.2 is another schematic diagram of location combination of a first detection region and a second detection region disclosed in an embodiment of the present invention;

FIG. 2.3 is still another schematic diagram of location combination of a first detection region and a second detection region disclosed in an embodiment of the present invention;

FIG. 3.1 is a schematic structural diagram of UE when an enabling switch of an ECG detection circuit is a force touch module disclosed in an embodiment of the present invention;

FIG. 3.2 is a schematic structural diagram of UE when an enabling switch of an ECG detection circuit is a physical button disclosed in an embodiment of the present invention; and FIG. 4 is a simplified block diagram of functional units of a blood pressure parameter detection apparatus disclosed in a unit apparatus embodiment of the present invention.

DESCRIPTION OF EMBODIMENTS

Figure 2:
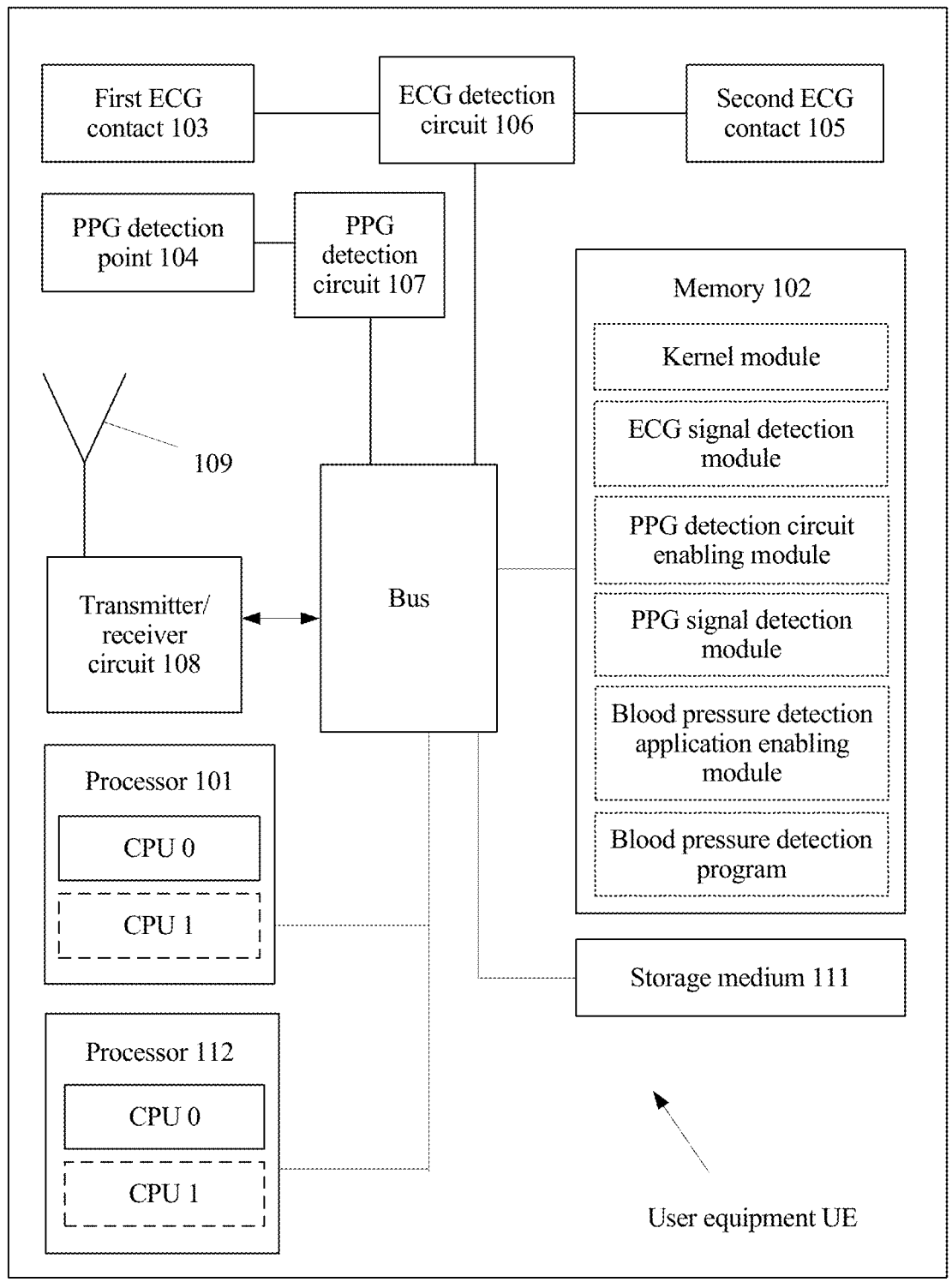
FIG. 2 is a simplified structural block diagram of composition of user equipment UE 100 that is disclosed in an embodiment of the present invention and to which a blood pressure parameter detection method disclosed in an embodiment of the present invention is applied.

Embodiments of the present invention provide a blood pressure detection method and user equipment, so as to improve blood pressure detection convenience and accuracy of the user equipment, and improve user experience.

To make a person skilled in the art understand the technical solutions in the present invention better, the following clearly describes the technical solutions in the embodiments of the present invention with reference to the accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

In the specification, claims, and accompanying drawings of the present invention, the terms "first", "second", "third", "fourth", and so on are intended to distinguish between different objects but do not indicate a particular order. Moreover, the terms "include", "have", and any other variant thereof are intended to cover a non-exclusive inclusion. For example, a process, a method, a system, a product, or a device that includes a series of steps or units is not limited to the listed steps or units, but optionally further includes an unlisted step or unit, or optionally further includes another inherent step or unit of the process, the method, the product, or the device.

The following separately provides detailed descriptions.

To facilitate understanding of the embodiments of the present invention, the following first describes a blood pressure detection principle related to the embodiments of the present invention. Blood pressure is pressure of circulating blood on walls of blood vessels. The blood pressure is an important physiological parameter that reflects a circulatory function of a human body, and can indirectly reflect a pump function of the heart, periphery vascular resistance, a heart rhythm, aorta elasticity, a whole-body blood volume, a blood physical status, and the like. Currently, a non-invasive continuous blood pressure measurement method using a sensor is mainly a pulse wave velocity measurement method. The pulse wave velocity measurement method is put forward based on a characteristic of a linear relationship between a pulse wave transit velocity and arterial blood pressure. An arterial blood pressure value is indirectly calculated according to a measured pulse wave velocity (Pulse wave velocity, PWV) value, and the pulse wave velocity is calculated according to a pulse wave transit time (Pulse wave transit time, PWTT) between two points in the artery. If a distance between the two points remains unchanged, the PWV is inversely proportional to the PWTT. Therefore, the arterial blood pressure value can be indirectly calculated according to the PWTT. The PWTT is a time for pulse wave transit from a point of a proximal end to another point of a distal end in the human artery and is a non-invasive parameter that can reflect a sudden change of blood pressure. In a pulse wave transit time measurement method, basically, time delays of signals in an electrocardiogram (electrocardiogram, ECG for short) and a photoplethysmogram (PPG) are synchronously detected, that is, continuous detection is performed by combining one channel of ECG and one channel of PPG. As shown in FIG. 1.1, generally, a time difference between an R-wave peak point of the ECG and a rising point of an ascending branch of the PPG is used as the PWTT. When a distance is fixed, the PWTT is inversely proportional to the PWV. Therefore, when the distance is fixed, the PWV may be calculated according to the PWTT.

The electrocardiogram ECG is a graph of electric potential changes from the body surface in multiple forms that are recorded by an electrocardiograph. In each cardiac cycle, pacemakers, atriums, and ventricles are successively excited with changes of electrocardiogram bioelectricity. In an excitation process of the heart, a biopower appears, a current is generated, and the current flows within periphery tissues. Therefore, a time-varying electric potential difference of the current may be measured by using a pair of electrodes (for example, a pair of detection electrodes formed by a first ECG contact and a second ECG contact described in this embodiment of the present invention) outside the heart. Photoplethysmogram (photoplethysmography, PPG) is a non-invasive detection method for detecting a blood volume change in a living tissue by means of photoelectricity according to a Lambert Beer law and a light scattering theory. When a beam of a particular wavelength reaches a fingertip skin surface, the beam is transmitted to a photoelectric receiver by means of transmission or reflection. In this process, because the beam is absorbed and attenuated by the fingertip skin, muscles, and blood, light intensity detected by a detector is attenuated. Absorption of light by skin, muscles, tissues, and the like remains unchanged in the whole blood circulation, and a blood volume within the skin changes in a pulsatile manner under influence of the heart. During systole, a periphery blood volume is largest, light absorption is also largest, and detected light intensity is weakest. During diastole, on the contrary, detected light intensity is strongest. Light intensity received by a light receiver changes in a pulsatile manner. A light intensity change signal is converted into an electric signal, and a change of a pulse blood volume may be obtained. To obtain a PPG signal, a photoelectric sensor is usually used for collection. The photoelectric sensor includes a light emitting diode (a light emitting tube) and a phototransistor (a receiving tube), and includes a transmissive photoelectric sensor and a reflective photoelectric sensor, as shown in FIG. 1.2. A measurement manner in which the light emitting diode and the phototransistor are disposed on a same side of a measured tissue is a reflective manner. Incident light is received by the phototransistor on the same side as the light emitting diode after being scattered by a tissue. A PPG detection point described in this embodiment of the present invention may be, for example, the reflective photoelectric sensor.

Further, referring to FIG. 2, FIG. 2 is a simplified structural block diagram of composition of user equipment UE 100 to which a blood pressure parameter detection method disclosed in an embodiment of the present invention is applied. As shown in FIG. 2, the UE 100 includes a processor 101, and the processor 101 may be coupled to one or more data storage media. The data storage media may include a storage medium storage medium 111 and at least one memory unit 102. The storage medium 111 may be read-only, for example, a read-only memory ROM, or may be readable/writable, for example, a hard disk or a flash memory. The memory 102 may be, for example, a random access memory RAM. The memory 102 may be combined with the processor 101, or may be integrated into the processor 101, or include one independent unit or multiple units.

The processor 101 is a control center of the UE 100 and is specifically configured to: execute an instruction, complete an interrupt event, and provide a time function and time series of multiple other functions, and processing equipment. Optionally, the processor 101 includes one or more central processing units CPUs, for example, a CPU 0 and a CPU 1 shown in FIG. 2. Optionally, the UE 100 may further include multiple processors, for example, a processor 101 and a processor 112 shown in FIG. 2. Each processor may be single-core or multi-core. Unless otherwise specified, a specific implementation of the processor or the memory described in the present invention includes a universal component or a dedicated component. The universal component is configured to execute a task at a specific moment, and the dedicated component is produced to execute a dedicated task. The processor described in this embodiment of the present invention may include at least one electronic device, a circuit, and/or a processor chip configured to process data (for example, a computer program instruction).

Program code executed by the processor 101 and/or the processor 112, or a single CPU in the processor 101 and/or the processor 112 may be stored in the memory 102 or the storage medium 111. Optionally, program code (for example, an ECG signal detection module) stored in the storage medium 111 may be copied to the memory 102, so that the processor runs the program code. The processor runs at least one kernel module (for example, a kernel module in open operating systems that include the following trademarks: LINUX™, WINDOWS™, ANDROID™, IOS™, and the like), and the kernel module is configured to: control running of another program in the UE 100, control communication with an external device, and control use of device resources.

The UE 100 further includes a first ECG contact 103, a PPG detection point 104, a second ECG contact 105, an ECG detection circuit 106 connected to the first ECG contact 103 and the second ECG contact 105, and a PPG detection circuit 107 connected to the PPG detection point. Detection electrodes formed by the first ECG contact 103 and the second ECG contact 105 are configured to detect an ECG signal of a user. The PPG detection point is configured to detect a PPG signal of the user. Specifically, the ECG detection circuit 106 and the PPG detection circuit 107 may include a primary amplification circuit, a high-pass filtering circuit, a low-pass cascade circuit, a second-order amplification circuit, a potential translation circuit, and the like.

Optionally, an area of a first detection region formed by the PPG detection point 104 and the first ECG contact 103 is less than a preset area threshold. The second ECG contact 105 is disposed in a second detection region of the UE 100, and the first detection region is different from the second detection region. For example, the preset area may be an average area of fingertip surfaces of adults, so that a user can simultaneously touch the PPG detection point and the first ECG contact by using only one finger. Such setting helps reduce a quantity of touch locations between the user and detection points and improve stability of touching the ECG detection points and the PPG detection point by the user, thereby improving blood pressure parameter detection accuracy of the UE.

It may be understood that the first detection region and the second detection region may be combined in various forms.

In an embodiment, as shown in FIG. 2.1, the first detection region may be on an upper frame of the UE 100, and the second detection region may be on a lower frame of the UE 100. The upper frame and the lower frame are preferably made of metal materials.

In another embodiment, as shown in FIG. 2.2, the first detection region may be at a location of a fingerprint recognition module (for example, a Home button location, a location directly below a rear camera of a mobile phone) of the UE 100, and the second detection region may be on an upper frame of the UE 100. The first ECG contact 103 and the PPG detection point 104 may be disposed in the fingerprint recognition module of the UE 100. The first ECG contact 103 may be specifically disposed on a metal drive ring or a metal frame of the fingerprint recognition module, and the PPG detection point 104 may be specifically disposed in a radiofrequency sensing electrode array of the fingerprint recognition module.

In still another embodiment, as shown in FIG. 2.3, the first detection region may be at a preset location near an earpiece of the UE 100, and the second detection region may be on a side frame of the UE 100. When the user answers a call, and a palm of the user touches the side frame of the UE 100, the palm of the user can touch the second detection region, and a part (for example, an earlobe) of an ear of the user can touch the first detection region at the same time.

It may be understood that a solution in which the area of the first detection region is less than the preset area threshold is merely a preferred implementation solution. A detection location of the PPG detection point 104 and a detection location of the first ECG contact 103 may be two locations that are relatively far from each other on the UE 100. The detection location of the PPG detection point 104 and the detection location of the first ECG contact 103 are not uniquely limited in the present invention.

Optionally, the UE 100 may further include a receiver/transmitter circuit 108 and an antenna 109, and the receiver/transmitter circuit 108 and the antenna 109 are configured to implement connection between the UE 100 and an external network. Components of the UE 100 may be coupled by using a communications bus, and the bus includes at least one of the following: a data bus, an address bus, a control bus, an extended bus, or a local bus.

It should be noted that the UE 100 is merely an example of an entity apparatus form disclosed in this embodiment of the present invention. The UE 100 described in this embodiment of the present invention may be an electronic device on which a blood pressure detection application is installed, for example, a smartphone, a tablet computer, a wearable device, or a notebook computer. An entity apparatus form of the UE is not uniquely limited in this embodiment of the present invention.

As shown in FIG. 2, the memory 102 in the UE 100 stores a to-be-run program. The program specifically includes a kernel module of an operating system of the UE and at least one software module (an ECG signal detection module, a PPG detection circuit enabling module, a PPG signal detection module, a blood pressure detection application enabling module, a blood pressure detection program, or the like). The UE 100 can run the program (and another program) to obtain a blood pressure parameter of the user.

The processor 101 of the UE 100 executes the ECG signal detection module in the memory 102 to detect an ECG signal of the user by using the first ECG contact and the second ECG contact that are connected to the ECG detection circuit 106 of the UE 100, where the first ECG contact and the second ECG contact form a pair of detection electrodes.

When determining that the detected ECG signal matches a prestored reference ECG signal, the processor 101 of the UE 100 executes the PPG detection circuit enabling module in the memory 102 to enable the PPG detection circuit of the UE.

The processor 101 of the UE 100 executes the PPG signal detection module in the memory 102 to detect a PPG signal of the user by using the PPG detection point connected to the PPG detection circuit.

When determining that the detected PPG signal matches a prestored reference PPG signal, the processor 101 of the UE 100 executes the blood pressure detection application enabling module in the memory 102 to enable the blood pressure detection application of the UE.

The processor 101 of the UE 100 invokes the blood pressure detection program in the memory 102 to process the detected ECG signal and the detected PPG signal by using the blood pressure detection application to obtain the blood pressure parameter of the user. The blood pressure detection program may specifically include a prestored PWTT calculation program and a blood pressure parameter calculation program. The PWTT calculation program may specifically include a beat-by-beat signal separation subprogram, a low-pass filtering subprogram, a baseline drift removing subprogram, a subprogram for detecting an R-wave peak point of an ECG signal, a subprogram for detecting a rising point of a PPG signal, a PWTT calculation subprogram, and the like. A blood pressure calculation formula included in the blood pressure calculation program may be specifically as follows:

$$DBP = \frac{SBP_o}{3} + \frac{2DBP_o}{3} + A\ln\left(\frac{PWTT_{W_o}}{PWTT_W}\right) - \frac{(SBP_o - DBP_o)}{3}\frac{PWTT_{W_o}^2}{PWTT_W^2};$$

$$\text{and } SBP = DBP + (SBP_o - DBP_o)\frac{PWTT_{W_o}^2}{PWTT_W^2},$$

where

DBP is diastolic blood pressure, $DBP_o$ is calibration diastolic blood pressure, SBP is systolic blood pressure, $SBP_o$ is calibration systolic blood pressure, PWTT is a pulse wave transit time, $PWTT_o$ is a calibration pulse wave transit time, and A is a constant.

It may be learned that UE first detects an ECG signal of a user by using a first ECG contact and a second ECG contact; next, when determining that the detected ECG signal matches a prestored reference ECG signal, the UE enables a PPG detection circuit of the UE, and detects a PPG signal of the user by using a PPG detection point connected to the PPG detection circuit; then, when determining that the detected PPG signal matches a prestored reference PPG signal, the UE enables a blood pressure detection application of the UE, and processes the detected ECG signal and the detected PPG signal by using the blood pressure detection application to obtain a blood pressure parameter of the user.

In the foregoing blood pressure parameter detection process of the UE, when detecting that the obtained ECG signal matches the prestored reference ECG signal, the UE may enable the PPG detection circuit of the UE, and when detecting that the obtained PPG signal matches the prestored reference PPG signal, the UE may enable the blood pressure detection application of the UE. It may be learned that in the foregoing blood pressure parameter detection process of the UE, the user does not need to perform complex setting operations, thereby improving blood pressure detection convenience of the UE.

In addition, in the foregoing blood pressure detection process, the UE needs to detect that the obtained ECG signal matches the prestored reference ECG signal, so as to enable the PPG detection circuit, and needs to detect that the obtained PPG signal matches the prestored reference PPG signal, so as to enable the blood pressure detection application of the UE. The matched ECG signal and the matched PPG signal are corresponding to a state in which the user steadily touches the ECG detection points and the PPG detection point, so that both the ECG signal and the PPG signal processed after the UE enables the blood pressure detection application are signals obtained when the user steadily touches a detection point. Therefore, error signals entered by the user in an unsteady touch state can be reduced, thereby improving blood pressure detection accuracy of the UE.

Optionally, the UE 100 further includes an enabling switch of the ECG detection circuit 106, and the enabling switch includes at least one of the following: a force touch module, a physical button, or a fingerprint recognition module. Before the processor detects the ECG signal of the user by using the first ECG contact 103 and the second ECG contact 105 that are connected to the ECG detection circuit 106 of the UE 100, the processor 101 is further configured to:

detect an enabling operation instruction that is of the user and for the enabling switch of the ECG detection circuit 106 of the UE 100; and enable the ECG detection circuit 106 when detecting the enabling operation instruction that is of the user and for the enabling switch of the ECG detection circuit 106 of the UE 100.

The software module may include one or more instruction sets. By executing the one or more instruction sets, the UE performs one or more substeps consistent with the described functions. These substeps are described in detail in the subsequent method embodiment of the present invention.

Consistent with the foregoing technical solution, a method embodiment of the present invention discloses a blood pressure parameter detection method. It should be noted that the blood pressure parameter detection method disclosed in this method embodiment can be implemented by an entity apparatus such as the example UE 100 shown in FIG. 2, but the example UE 100 constitutes no unique limitation on the blood pressure parameter detection method disclosed in this method embodiment of the present invention.

Figure 3:
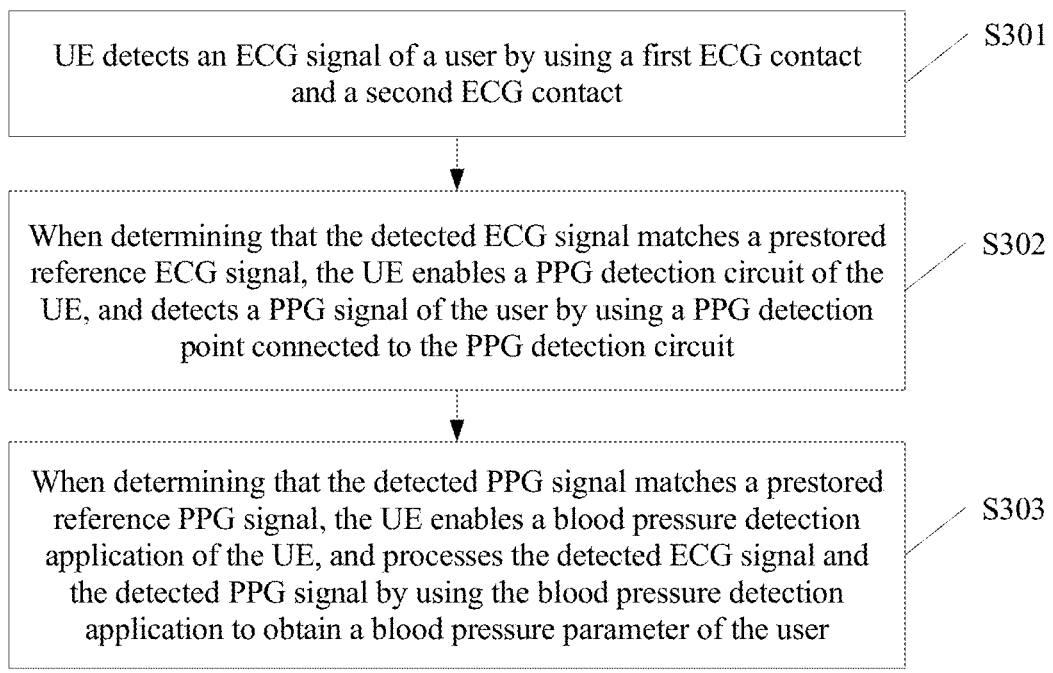
FIG. 3 is a schematic flowchart of a blood pressure parameter detection method disclosed in an embodiment of the present invention.

As shown in FIG. 3, the blood pressure parameter detection method disclosed in this method embodiment includes the following steps.

S301. UE detects an ECG signal of a user by using a first ECG contact and a second ECG contact that are connected to an ECG detection circuit of the UE.

S302. When determining that the detected ECG signal matches a prestored reference ECG signal, the UE enables a PPG detection circuit of the UE, and detects a PPG signal of the user by using a PPG detection point connected to the PPG detection circuit.

In this embodiment of the present invention, the prestored reference ECG signal may include multiple ECG signals that are pre-recorded by the user in different conditions such as different statuses and different time periods, or may be multiple ECG signals that are for different user groups and that are prestored by developers at delivery of the UE, or may be multiple ECG signals that are pushed by a cloud server and that match a physiological parameter of the user. For example, the physiological parameter of the user may be a gender or an age.

In a specific implementation, for example, a specific manner in which the UE determines that the detected ECG signal matches the prestored reference ECG signal may be as follows:

The UE extracts a feature signal from the detected ECG signal, and processes the extracted feature signal to obtain an electric potential difference (an absolute value is taken). If the electric potential difference matches an electric potential difference extracted from the prestored reference ECG signal, the UE determines that the detected ECG signal matches the prestored reference ECG signal.

Alternatively, the UE draws an amplitude-time waveform graph of the ECG signal based on the detected ECG signal. If the waveform graph matches an amplitude-time waveform graph of the prestored reference ECG signal (for example, periods are close and waveform changes match), the UE determines that the detected ECG signal matches the prestored reference ECG signal.

S303. When determining that the detected PPG signal matches a prestored reference PPG signal, the UE enables a blood pressure detection application of the UE, and processes the detected ECG signal and the detected PPG signal by using the blood pressure detection application to obtain a blood pressure parameter of the user.

In this embodiment of the present invention, for example, a specific manner in which the UE determines that the detected PPG signal matches the prestored reference PPG signal may be as follows:

The UE extracts a feature signal from the detected PPG signal, and processes the extracted feature signal to obtain an amplitude difference (an absolute value is taken). If the amplitude difference matches an amplitude difference extracted from the prestored reference PPG signal, the UE determines that the detected PPG signal matches the prestored reference PPG signal.

Alternatively, the UE draws an amplitude-time waveform graph of the PPG signal based on the detected PPG signal. If the waveform graph matches an amplitude-time waveform graph of the prestored reference PPG signal (for example, periods are close and waveform changes match), the UE determines that the detected PPG signal matches the prestored reference PPG signal.

When the UE enables the blood pressure detection application of the UE, a display status and display content of a display screen of the UE may be diverse.

In an embodiment, when the UE enables the blood pressure detection application of the UE, the display screen of the UE may be in a screen-off state, that is, the UE in a standby state may directly enable the blood pressure detection application in the background, thereby improving blood pressure detection convenience of the UE.

In another embodiment, when the UE enables the blood pressure detection application of the UE, the display screen of the UE may be in a screen-on state, and the display screen may specifically display an application screen of the blood pressure detection application or display another application program currently running on the UE.

For example, when the user is in a call, a display interface of the UE displays contact information of a calling party, and the UE may enable the blood pressure detection application in the background.

For another example, the display screen of the UE is in a screen-off state, and when determining that the detected PPG signal matches the prestored reference PPG signal, the UE lights up the screen and enables the blood pressure detection application. The UE may further output, on the display screen, prompt information that is used to remind the user that blood pressure is being measured, or the like; the UE may further display a real-time change diagram of blood pressure on the display screen, for example, display blood pressure parameters of the user in a number scrolling manner; or the UE may further display, on the display screen, a blood pressure measurement interaction diagram of the UE and the user, to remind the user to steadily touch the ECG contacts and the PPG detection point. This helps obtain an accurate blood pressure detection result.

The detected ECG signal and the detected PPG signal may be specifically stored in a cache of the UE in a converged signal form. For example, a specific manner in which the UE processes the detected ECG signal and the detected PPG signal by using the blood pressure detection application to obtain the blood pressure parameter of the user may be as follows:

The UE first processes an obtained converged signal according to a prestored pulse wave transit time PWTT calculation policy to obtain a PWTT, and then the UE calculates the blood pressure parameter of the user according to the PWTT and a prestored blood pressure calculation policy.

In a specific implementation, a specific manner in which the UE processes the obtained converged signal according to the prestored pulse wave transit time PWTT calculation policy to obtain the PWTT is as follows:

The UE first performs beat-by-beat separation on the obtained converged signal, to obtain a separated ECG signal and a separated PPG signal. Next, the UE separately performs high-frequency noise filtering processing on the separated ECG signal and the separated PPG signal, to obtain a noise-reduced ECG signal and a noise-reduced PPG signal. Then, the UE separately performs baseline drift removing on the noise-reduced ECG signal and the noise-reduced PPG signal, to obtain a baseline-drift-removed ECG signal and a baseline-drift-removed PPG signal. Then, the UE separately processes the baseline-drift-removed ECG signal and the baseline-drift-removed PPG signal based on a prestored differential threshold algorithm, to obtain an R-wave peak point of the ECG signal and a rising edge inflection point of the PPG signal. Finally, the UE determines the PWTT based on the determined R-wave peak point of the ECG signal and the determined rising edge inflection point of the PPG signal.

It may be learned that in this embodiment of the present invention, UE first detects an ECG signal of a user by using a first ECG contact and a second ECG contact; next, when determining that the detected ECG signal matches a prestored reference ECG signal, the UE enables a PPG detection circuit of the UE, and detects a PPG signal of the user by using a PPG detection point connected to the PPG detection circuit; then, when determining that the detected PPG signal matches a prestored reference PPG signal, the UE enables a blood pressure detection application of the UE, and processes the detected ECG signal and the detected PPG signal by using the blood pressure detection application to obtain a blood pressure parameter of the user.

In the foregoing blood pressure parameter detection process of the UE, when detecting that the obtained ECG signal matches the prestored reference ECG signal, the UE may enable the PPG detection circuit of the UE, and when detecting that the obtained PPG signal matches the prestored reference PPG signal, the UE may enable the blood pressure detection application of the UE. It may be learned that in the foregoing blood pressure parameter detection process of the UE, the user does not need to perform complex setting operations, thereby improving blood pressure detection convenience of the UE.

In addition, in the foregoing blood pressure detection process, the UE needs to detect that the obtained ECG signal matches the prestored reference ECG signal, so as to enable the PPG detection circuit, and needs to detect that the obtained PPG signal matches the prestored reference PPG signal, so as to enable the blood pressure detection application of the UE. The matched ECG signal and the matched PPG signal are corresponding to a state in which the user steadily touches the ECG detection points and the PPG detection point, so that both the ECG signal and the PPG signal processed after the UE enables the blood pressure detection application are signals obtained when the user steadily touches a detection point. Therefore, error signals entered by the user in an unsteady touch state can be reduced, thereby improving blood pressure detection accuracy of the UE.

Optionally, in this embodiment of the present invention, before the UE detects the electrocardiogram ECG signal of the user by using the first ECG contact and the second ECG contact that are connected to the ECG detection circuit of the UE in step S301, the UE may further perform the following operations:

detecting, by the UE, an enabling operation instruction that is of the user and for an enabling switch of the ECG detection circuit of the UE, where the ECG detection circuit connects the first ECG contact and the second ECG contact, and the enabling switch of the ECG detection circuit includes at least one of the following: a force touch module, a physical button, or a fingerprint recognition module; and enabling, by the UE, the ECG detection circuit when detecting the enabling operation instruction that is of the user and for the enabling switch of the ECG detection circuit of the UE.

In a specific implementation, if the enabling switch of the ECG detection circuit includes the force touch module of the UE, a specific manner in which the UE detects the enabling operation instruction that is of the user and for the enabling switch of the ECG detection circuit of the UE is as follows: The UE detects that a force parameter entered by the user by using the force touch module matches a preset force parameter.

For example, as shown in FIG. 3.1, the force touch module of the UE may be specifically disposed directly below a rear camera of the UE. The first ECG contact is disposed on a metal frame of the force touch module, the PPG detection point is disposed in a force sensor array of the force touch module, and the second ECG contact is disposed at a preset location on a side frame of the UE. It is assumed that the preset force parameter is a force interval from 5 N to 10 N (this interval helps the user to steadily touch the first ECG contact and the PPG detection point of the force touch module). When the user is taking a photo, a finger of the user presses and holds the force touch module. When detecting that the force parameter entered by the user by using the force touch module is 7.4 N, the UE enables the ECG detection circuit of the UE.

In a specific implementation, if the enabling switch of the ECG detection circuit includes the physical button that is disposed at a preset location of the UE and that is configured to enable the ECG detection circuit, a specific manner in which the UE detects the enabling operation instruction that is of the user and for the enabling switch of the ECG detection circuit of the UE is as follows: The UE captures an enabling operation event that is of the user and for the physical button, where the physical button is disposed at the preset location of the UE and configured to enable the ECG detection circuit.

For example, as shown in FIG. 3.2, the physical button that is disposed at the preset location of the UE and that is configured to enable the ECG detection circuit is specifically disposed on an upper frame of the UE and is close to a headset jack. A specific form of the physical button may be, for example, a contact switch (a press operation is corresponding to an enabling operation event of the ECG detection circuit), a joystick (a toggle operation is corresponding to an enabling operation event of the ECG detection circuit), or a knob (a rotation operation is corresponding to an enabling operation event of the ECG detection circuit). An indicator may be further disposed near the physical button, and the indicator can visually show an enabling work state and a disabling work state of the ECG detection circuit.

In a specific implementation, if the enabling switch of the ECG detection circuit includes the fingerprint recognition module of the UE, a specific manner in which the UE detects the enabling operation instruction that is of the user and for the enabling switch of the ECG detection circuit of the UE is as follows: The UE detects that fingerprint data entered by the user by using the fingerprint recognition module matches preset fingerprint data. After identifying the fingerprint data of the user, the UE may determine a current user identity, and the blood pressure parameter detected by the UE can be accurately uploaded to a database related to the determined user identity.

For example, as shown in FIG. 2.2, the fingerprint recognition module of the UE is disposed at a Home button location below the display screen on the front of the UE. If the UE detects that the fingerprint data entered by the user by using the fingerprint recognition module matches the preset fingerprint data, the UE enables the ECG detection circuit.

In addition, it should be noted that in this embodiment of the present invention, a switch status of the ECG detection circuit may be flexibly set according to a preset enabling policy. The enabling switch of the ECG detection circuit described in the optional embodiment may be an optional solution when the preset enabling policy is that the ECG detection circuit is always off. Obviously, when the preset enabling policy is that the ECG detection circuit is always on, the enabling switch for enabling the ECG detection circuit may not disposed in the UE.

Further, optionally, after obtaining the blood pressure parameter of the user, the UE may further perform the following operation:

broadcasting, by the UE by using a speaker, the blood pressure parameter that is of the user and that is detected this time; or displaying, by the UE on the display screen of the UE, the blood pressure parameter that is of the user and that is detected this time; or uploading, by the UE to a server, physiological data that carries a user identity or a UE identity (for example, a SIM card number and a user name) and the blood pressure parameter that is of the user and that is detected this time, where the server end may further share the physiological data with several pre-bound terminal devices, or transmit the physiological data to a medical service information management system, so as to analyze the blood pressure parameter of the user to monitor a physiological status of the user.

Further, optionally, in this embodiment of the present invention, in a specific implementation process in which the UE enables the PPG detection circuit of the UE, the UE may reuse the enabling switch that is for enabling the ECG detection circuit and that is described in the foregoing optional embodiment (only when the enabling switch is merged with the first ECG contact and the PPG detection point). For example, an enabling switch of the force touch module is reused. That is, after determining that the detected PPG signal matches the prestored reference PPG signal, the UE continues to detect whether the force parameter entered by the user by using the force touch module matches the preset force parameter. If the force parameter entered by the user by using the force touch module matches the preset force parameter, the UE enables the PPG detection circuit. If the force parameter entered by the user by using the force touch module does not match the preset force parameter, the UE may output prompt information used to remind the user to steadily touch the first detection region and the second detection region. In this way, this helps the user to steadily touch the first detection region and the second detection region, thereby improving blood pressure detection accuracy.

Some or all steps performed by the UE may be specifically implemented by the UE by executing the software module. For example, step S301 may be implemented by the UE by executing the ECG signal detection module shown in FIG. 2, step S302 may be implemented by the UE by executing the PPG circuit enabling module and the PPG signal detection module shown in FIG. 2, and step S303 may be implemented by the UE by executing the blood pressure detection application enabling module shown in FIG. 2 and invoking the blood pressure detection program.

The blood pressure parameter detection method described in this method embodiment of the present invention may be implemented by an apparatus disclosed in a functional unit apparatus embodiment described below. The apparatus includes a blood pressure parameter detection apparatus shown in FIG. 4, and the blood pressure parameter detection apparatus can implement steps of the method described in FIG. 3.

As shown in FIG. 4, FIG. 4 is a simplified block diagram of functional units of a blood pressure parameter detection apparatus 400 disclosed in a function apparatus embodiment of the present invention. The blood pressure parameter detection apparatus 400 includes an ECG signal detection unit 401, an ECG circuit enabling unit 402, a PPG signal detection unit 403, a blood pressure detection application enabling unit 404, and a signal processing unit 405.

The ECG signal detection unit 401 is configured to detect an electrocardiogram ECG signal of a user by using a first ECG contact and a second ECG contact that are connected to an ECG detection circuit of the UE, where the first ECG contact and the second ECG contact form a pair of detection electrodes.

The ECG circuit enabling unit 402 is configured to enable a photoplethysmogram PPG detection circuit when it is determined that the ECG signal detected by the ECG signal detection unit 401 matches a prestored reference ECG signal.

The PPG signal detection unit 403 is configured to detect a PPG signal of the user by using a PPG detection point connected to the PPG detection circuit.

The blood pressure detection application enabling unit 404 is configured to enable a blood pressure detection application when it is determined that the PPG signal detected by the PPG signal detection unit 403 matches a prestored reference PPG signal.

The signal processing unit 405 is configured to process the detected ECG signal and the detected PPG signal by using the blood pressure detection application to obtain a blood pressure parameter of the user.

Optionally, the blood pressure parameter detection apparatus further includes:

a switch enabling detection unit 406, configured to: before the ECG signal detection unit detects the electrocardiogram ECG signal of the user by using the first ECG contact and the second ECG contact that are connected to the ECG detection circuit of the UE, detect an enabling operation instruction that is of the user and for an enabling switch of the ECG detection circuit of the UE, where the ECG detection circuit connects the first ECG contact and the second ECG contact, and the enabling switch of the ECG detection circuit includes at least one of the following: a force touch module, a physical button, or a fingerprint recognition module; and an ECG detection circuit enabling unit 407, configured to enable the ECG detection circuit when the switch enabling detection unit detects the enabling operation instruction that is of the user and for the enabling switch of the ECG detection circuit of the UE.

It should be noted that the blood pressure parameter detection apparatus 400 described in the functional unit apparatus embodiment of the present invention is presented in a form of a functional unit. A meaning of the term "unit" used herein should be understood as wide as possible. An object for implementing a function of each "unit" may be, for example, an application-specific integrated circuit ASIC, a single circuit, a processor (a shared or dedicated chip set) for executing one or more software or firmware programs, a memory, a combinational logic circuit, and/or another suitable component for implementing the foregoing function.

For example, a person skilled in the art may know that a component form of a hardware carrier of the blood pressure parameter detection apparatus 400 may be specifically the UE 100 shown in any one of FIG. 2, FIG. 2.1, FIG. 2.2, FIG. 2.3, FIG. 3.1, or FIG. 3.2.

A function of the ECG signal detection unit 401 may be implemented by the processor 101, the memory 102, the first ECG contact 103, the second ECG contact 105, and the ECG detection circuit 106 in the UE 100. Specifically, the processor 101 executes the ECG signal detection module in the memory 102 to detect the ECG signal of the user by using the ECG detection circuit 106, the first ECG contact 103, and the second ECG contact 105.

A function of the ECG circuit enabling unit 402 may be implemented by the processor 101, the memory 102, and the PPG detection circuit 107 in the UE 100. Specifically, the processor 101 executes the ECG circuit enabling unit 402 in the memory 102 to enable the PPG detection circuit 107.

A function of the PPG signal detection unit 403 may be implemented by the processor 101, the memory 102, the PPG detection circuit 107, and the PPG detection point 104 in the UE 100. Specifically, the processor 101 executes the PPG signal detection module in the memory 102 to detect the PPG signal of the user by using the PPG detection point 104 connected to the PPG detection circuit 107.

A function of the blood pressure detection application enabling unit 404 may be implemented by the processor 101 and the memory 102 in the UE 100. Specifically, the processor 101 executes the blood pressure detection application enabling module in the memory 102 to enable the blood pressure detection application.

A function of the signal processing unit 405 may be implemented by the processor 101 and the memory 102 in the UE 100. Specifically, the processor 101 executes the blood pressure detection program in the memory 102, and processes the detected ECG signal and the detected PPG signal to obtain the blood pressure parameter of the user.

It may be learned that in this embodiment of the present invention, UE first detects an ECG signal of a user by using a first ECG contact and a second ECG contact; next, when determining that the detected ECG signal matches a prestored reference ECG signal, the UE enables a PPG detection circuit of the UE, and detects a PPG signal of the user by using a PPG detection point connected to the PPG detection circuit; then, when determining that the detected PPG signal matches a prestored reference PPG signal, the UE enables a blood pressure detection application of the UE, and processes the detected ECG signal and the detected PPG signal by using the blood pressure detection application to obtain a blood pressure parameter of the user.

In the foregoing blood pressure parameter detection process of the UE, when detecting that the obtained ECG signal matches the prestored reference ECG signal, the UE may enable the PPG detection circuit of the UE, and when detecting that the obtained PPG signal matches the prestored reference PPG signal, the UE may enable the blood pressure detection application of the UE. It may be learned that in the foregoing blood pressure parameter detection process of the UE, the user does not need to perform complex setting operations, thereby improving blood pressure detection convenience of the UE.

In addition, in the foregoing blood pressure detection process, the UE needs to detect that the obtained ECG signal matches the prestored reference ECG signal, so as to enable the PPG detection circuit, and needs to detect that the obtained PPG signal matches the prestored reference PPG signal, so as to enable the blood pressure detection application of the UE. The matched ECG signal and the matched PPG signal are corresponding to a state in which the user steadily touches the ECG detection points and the PPG detection point, so that both the ECG signal and the PPG signal processed after the UE enables the blood pressure detection application are signals obtained when the user steadily touches a detection point. Therefore, error signals entered by the user in an unsteady touch state can be reduced, thereby improving blood pressure detection accuracy of the UE.

A person of ordinary skill in the art may understand that all or some of the steps of the methods in the embodiments may be implemented by a program instructing relevant hardware. The program may be stored in a computer readable storage medium. The storage medium may include a flash memory, a read-only memory (Read-Only Memory, ROM), a random access memory (Random Access Memory, RAM), a magnetic disk, an optical disc, and the like.

The foregoing describes in detail a blood pressure parameter detection method and user equipment disclosed in the embodiments of the present invention. In this specification, specific examples are used to describe the principle and implementations of the present invention, and the description of the embodiments is only intended to help understand the method and core idea of the present invention. Meanwhile, a person of ordinary skill in the art may, based on the idea of the present invention, make modifications with respect to the specific implementations and the application scope. Therefore, the content of this specification shall not be construed as a limitation to the present invention.

The invention claimed is:

1. A blood pressure parameter detection method, comprising:

detecting, by user equipment (UE), an electrocardiogram (ECG) signal of a user by using a first ECG contact and a second ECG contact that are connected to an ECG detection circuit of the UE, wherein the first ECG contact and the second ECG contact form a pair of detection electrodes;

determining that the detected ECG signal matches a pre-stored reference ECG signal;

after determining that the detected ECG signal matches a pre-stored reference ECG signal, enabling, by the UE, a photoplethysmogram (PPG) detection circuit, and detecting a PPG signal of the user by using a PPG detection point connected to the PPG detection circuit;

determining that the detected PPG signal matches a pre-stored reference PPG signal; and after determining that the detected PPG signal matches a pre-stored reference PPG signal, enabling, by the UE, a blood pressure detection application, and processing the detected ECG signal and the detected PPG signal by using the blood pressure detection application to obtain a blood pressure parameter of the user.

2. The blood pressure parameter detection method according to claim 1, wherein an area of a first detection region formed by the PPG detection point and the first ECG contact is less than a preset area threshold; and the second ECG contact is disposed in a second detection region of the UE, and the first detection region is different from the second detection region.

3. The blood pressure parameter detection method according to claim 1, wherein before detecting, by the UE, the ECG signal of a user by using the first ECG contact and the second ECG contact that are connected to an ECG detection circuit of the UE, the method further comprises:

detecting, by the UE, an enabling operation instruction from the user, the enabling operation instruction being for an enabling switch of the ECG detection circuit of the UE, wherein the ECG detection circuit connects the first ECG contact and the second ECG contact, and the enabling switch of the ECG detection circuit comprises at least one of the following: a force touch module, a physical button, or a fingerprint recognition module; and enabling, by the UE, the ECG detection circuit when the enabling operation instruction by the user is detected.

4. User equipment UE, comprising:

a memory for storing executable program code, a first electrocardiogram (ECG) contact, a second ECG contact, an ECG detection circuit connected to the first ECG contact and the second ECG contact, a photoplethysmogram (PPG) detection point, and a PPG detection circuit connected to the PPG detection point; and a processor coupled to the memory, the ECG detection circuit, and the PPG detection circuit; wherein the processor invokes the executable program code stored in the memory such that when the executable program code is invoked the processor is caused to perform:

detecting an ECG signal of a user by using the first ECG contact and the second ECG contact that are connected to the ECG detection circuit, wherein the first ECG contact and the second ECG contact form a pair of detection electrodes;

determining the detected ECG signal matches a pre-stored reference ECG signal;

after determining the detected ECG signal matches a pre-stored reference ECG signal, enabling the PPG detection circuit of the UE, and detecting a PPG signal of the user by using the PPG detection point connected to the PPG detection circuit;

determining the detected PPG signal matches a pre-stored reference PPG signal; and after determining the detected PPG signal matches a pre-stored reference PPG signal, enabling a blood pressure detection application of the UE, and processing the detected ECG signal and the detected PPG signal by using the blood pressure detection application to obtain a blood pressure parameter of the user.

5. The UE according to claim 4, wherein an area of a first detection region formed by the PPG detection point and the first ECG contact is less than a preset area threshold; and the second ECG contact is disposed in a second detection region of the UE, and the first detection region is different from the second detection region.

6. The UE according to claim 4, wherein the UE further comprises an enabling switch of the ECG detection circuit, and the enabling switch comprises at least one of the following: a force touch module, a physical button, or a fingerprint recognition module; and before the processor detects the ECG signal of the user by using the first ECG contact and the second ECG contact that are connected to the ECG detection circuit of the UE, the processor is further configured to:

detect an enabling operation instruction from the user, the enabling operation instruction being for the enabling switch of the ECG detection circuit of the UE; and enable the ECG detection circuit when the enabling operation instruction from the user is detected.

* * * * *